United States Patent [19]

Mackal

[11] Patent Number: 5,284,475
[45] Date of Patent: Feb. 8, 1994

[54] LUER VALVE ADAPTER WITH EXPANDABLE END

[76] Inventor: Glenn H. Mackal, 2586 25th Ave., No. St. Petersburg, Fla. 33713

[21] Appl. No.: 92,629

[22] Filed: Jul. 15, 1993

Related U.S. Application Data

[63] Continuation-in-part of Ser. No. 918,346, Jul. 21, 1992.

[51] Int. Cl.⁵ .................. A61M 5/00; F16K 51/00
[52] U.S. Cl. ..................... 604/247; 604/283; 251/150; 251/342
[58] Field of Search ............. 604/83, 99, 167, 236, 604/240, 243, 247, 249, 256, 283; 251/149.1, 150, 149.7, 342; 137/843

[56] References Cited

U.S. PATENT DOCUMENTS

| 3,831,629 | 8/1974 | Mackal et al. | 604/99 |
|---|---|---|---|
| 4,135,501 | 1/1979 | Leunissan | 285/8 |
| 4,240,425 | 12/1980 | Akhai | 604/243 |
| 4,429,856 | 2/1984 | Jackson | 604/283 |
| 4,449,693 | 5/1984 | Gereg | 604/236 |

Primary Examiner—John D. Yasko
Assistant Examiner—Anthony Gutowski
Attorney, Agent, or Firm—Joseph C. Mason, Jr.; Ronald E. Smith

[57] ABSTRACT

A tubular adapter and check valve for Luer fittings. The end of the adapter that receives the Luer fitting is expandable radially outwardly in a substantially uniform manner so that Luer fittings of all sizes are snugly received by the adapter. Deep longitudinally extending grooves are formed in the adapter to provide the expandability. The adapter, when in repose, is designed to tightly receive the smallest in diameter Luer fittings, but it receives even the largest Luer fittings when in its expanded configuration. The adapter is also improved by providing radially inwardly extending fingers that hold a check valve in the adapter against axial displacement and by providing an annular shoulder that limits the depth of insertion of the Luer fitting into the adapter, which shoulder prevents over distortion of the check valve.

4 Claims, 2 Drawing Sheets

LUER VALVE ADAPTER WITH EXPANDABLE END

This is a continuation-in-part of copending U.S. patent application Ser. No. 07/918,346 filed on Jul. 21, 1992.

BACKGROUND OF THE INVENTION

1. Field of the Invention

This invention relates, generally, to medical appliances. More particularly, it relates to an adapter having utility in connection with Luer valves.

2. Description of the Prior Art

A Luer fitting or tip is a rigid, cylindrical-in-configuration, slightly tapered member that is formed on the leading end of the barrel of a common medical syringe. More particularly, it is a truncate tube that provides fluid communication between the interior of the barrel and the external environment.

Although it is mechanically possible to connect a catheter directly to a Luer fitting, such a direct connection is seldom made because non valved catheters use a rubber plug through which a needle is pushed. Just as importantly, such a direct connection is unvalved and there is usually a need for a valving function between a syringe and a catheter.

The Luer fitting and catheter are normally interconnected by an adapter member, known as a Luer valve, also of generally tubular construction, that firmly engages the catheter at a first end and the Luer fitting at a second end, thereby providing a reliable interconnection between the Luer fitting and the catheter.

The common adapter is provided with a check valve so that the contents of the barrel pass freely through the adapter into the catheter when the plunger of the syringe is advanced and so that reverse flow from the catheter to the barrel is not possible.

The adapter now in widespread use has a rigid plastic body and an elastomeric, slidably mounted check valve member disposed therein. Insertion of the Luer fitting into the second end of the adapter displaces the elastomeric check valve in an axial direction; this unseats the valve and permits fluid flow from the syringe barrel to the catheter. Part of the check valve is distorted or compressed as a result of the axial displacement, but the resiliency of said valve restores it to its undistorted configuration and hence to its seat when the Luer fitting is removed and reverse fluid flow is blocked. However, if the amount of distortion is too great, the check valve will not resume its position of repose, and unwanted reverse flow of fluid from the catheter may occur.

The prior art contains no teachings or suggestions that would advise one of ordinary skill in this art how to design the check valve of a Luer fitting adapter so that it is not subject to failure.

Although Luer fittings are important medical parts that are purportedly manufactured according to strict specifications, it is well known in the medical field that the respective diameters of a group of Luer fittings will vary widely. When the diameter of a Luer fitting is too small, it can easily withdraw from the adapter. When it is too large, it can break the adapter.

Between these two extremes, almost no Luer fitting is ever encountered that perfectly mates with its adapter. As a result, health care professionals have become accustomed to jamming together Luer fittings and their adapters, even though it is widely known that this can result in catastrophic failure of the medical procedure about to be undertaken. For example, if the elastomeric check valve within the adapter is overly distorted, as aforesaid, and fails to resume its flow-blocking position when the Luer fitting is withdrawn, the substance passing through the valve enters the balloon of the catheter. For example, sterile water would enter the balloon of a urinal catheter, and air would enter the balloon of an endotracheal tube.

Similarly, if the health care professional jams the Luer fitting and the adapter together, the check valve may not open fully in accordance with its design.

The inventors who have studied this problem in the past have all come up with the same solution: Improvements in the manufacture of Luer fittings designed to reduce the variations in dimensions of said fittings. This approach has not worked, because Luer fittings are made in vast quantities at high speed, and it is impractical to even hold out the hope that manufacturing tolerances can be improved to the degree needed.

There is a need for a better way to interconnect Luer fittings and catheters, but the prior art, when considered as a whole in accordance with the requirements of law, neither teaches nor suggests how this seemingly intractable problem could be overcome.

SUMMARY OF THE INVENTION

The present invention is an adapter for a Luer fitting that is free of the above-described limitations. The catheter end of the adapter is unchanged but the Luer fitting end thereof is substantially improved.

Specifically, the Luer fitting end is manufactured so that its diameter is slightly less than the diameter of the smallest Luer fitting. Being made of an elastomeric material, it gives slightly as required and snugly receives even the smallest in diameter Luer fitting. The novel adapter is made radially expandable, however, so that even the largest in diameter Luer fittings are also snugly received therewithin.

This expendability is achieved by thickening the cylindrical side walls of the Luer fitting end of the adapter and forming a plurality of longitudinally extending, circumstantially and equidistantly spaced grooves or flutes in the cylindrical walls of the adapter. In this manner, longitudinally extending, circumstantially and equidistantly spaced parts of the adapter are as thick or thicker than the unexpandable cylindrical walls of the rigid adapter heretofore known.

In a preferred embodiment, the circumferential extent of the grooves and of the intermediate ungrooved parts are substantially equal so that the overall structural integrity of the adapter is not sacrificed by the grooves formed therein.

Novel means in the form of radially extending fingers are also provided to insure that the resilient check valve member is not compressed beyond its elastic limit.

The primary object of this invention is to provide an adapter for interconnecting Luer fittings and catheters that snugly receives Luer fittings of widely varying diameters.

Another object is to provide an adapter having a check valve that is not subject to failure when distorted.

These and other important, objects, advantages, and features of the invention will become apparent as this description proceeds.

The invention accordingly comprises the features of construction, combination of elements and arrangement of parts that will be exemplified in the construction set forth hereinafter and the scope of the invention will be set forth in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
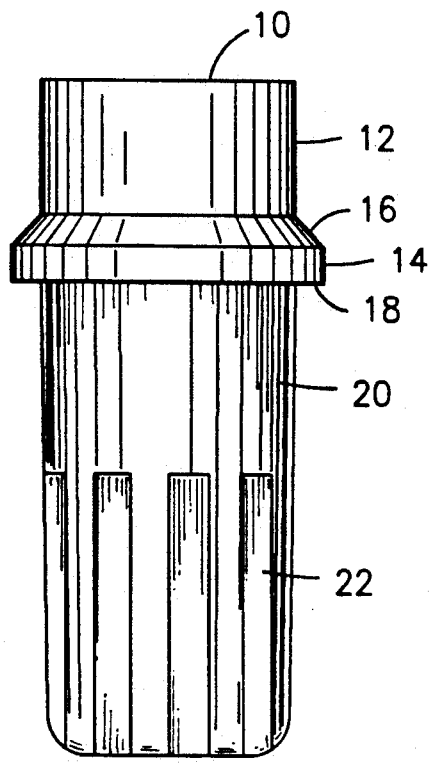
FIG. 1 is a side elevational view of an exemplary embodiment of the invention.

Referring now to FIG. 1, it will there be seen that an exemplary embodiment of the present invention is denoted as a whole by the reference numeral 10.

Adapter 10 has first part 12 adapted for substantially non-retractable engagement with a catheter, not shown. More particularly, an anti-retraction means 14 circumscribes adapter 10 as shown and prevents facile separation of said adapter and a catheter when the adapter is slide fittingly received within a catheter. Annular beveled surface 16 facilitates easy sliding entry of end 12 into a catheter, but annular surface 18, which projects orthogonally radially outwardly from the cylindrical surface of member 10, provides a catheter-gripping surface that firmly holds end 12 within said catheter. The grip can be overcome by the health care professional when separation of adapter 10 from the catheter is desired, but the grip prevents inadvertent separation. This gripping means is conventional and forms no part of the invention, per se.

The second end or second part of adapter 10 is denoted 20 as a whole. Plural longitudinally extending, equidistantly and circumstantially spaced grooves or flutes, collectively denoted 22, are formed in said second part 20, as perhaps best understood in connection with FIGS. 2 and 3.

Figure 2:
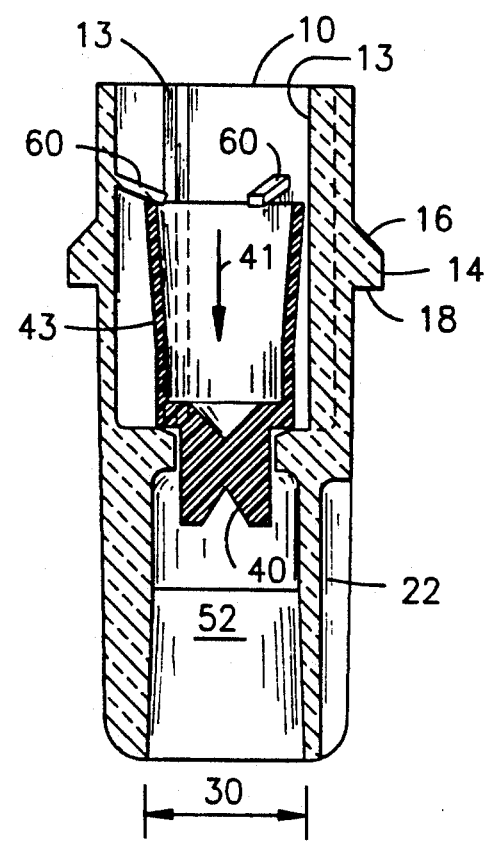
FIG. 2 is a longitudinal sectional view of the embodiment of FIG. 1.

The tubular side walls of part 20 are substantially thicker than the side walls of part 12, as clearly shown in FIG. 2. This important feature of the novel adapter 10 enables the formation therein of said grooves 22. The circumferential extent of each groove 22, denoted by double headed arrow 23 in FIG. 3, is about equal to the circumferential extent of the ungrooved side walls section 24 between grooves, denoted by double headed arrow 25 in said FIG.

Figure 3:
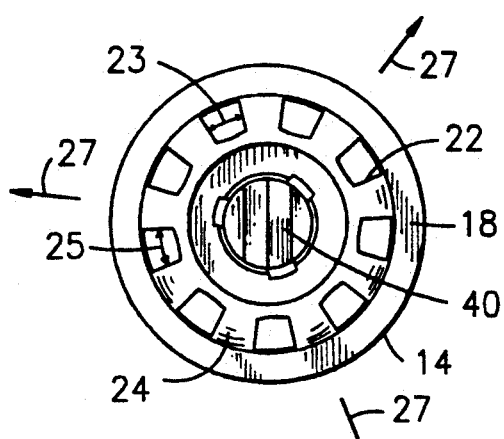
FIG. 3 is an end view of the device.
Figure 4:
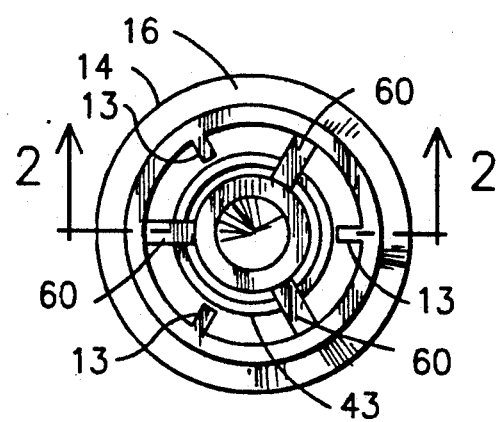
FIG. 4 is an end view of the opposite end of that depicted in FIG. 3.

This unique construction imparts radially outwardly directed expendability to part 20 as a whole, as indicated by the radially outwardly pointing directional arrows 27 in FIG. 3. The thickened or ungrooved parts 24 provide the needed structural integrity to the adapter 10.

Accordingly, adapter 10 is manufactured to have an inner diameter 30 (FIG. 2) that snugly receives Luer or similar fittings of the smallest diameter. Thus, when Luer fittings of larger diameters are used, the expendability provided by the grooves 22 enables second part 20 to expand radially outwardly in a substantially uniform manner to snug fittingly receive said larger in diameter Luer fittings. In this way, adapter 10 accepts all Luer fittings in a reliable way.

FIG. 2 also depicts a pliable check valve member 40 that is slidably mounted within tubular adapter 10. It is shown in its closed or seated position in that FIG.; when so seated, it blocks reverse fluid flow through adapter 10, i.e., fluid attempting to flow in the direction indicated by arrow 41 is blocked. This is the in repose configuration of adapter 10.

Figure 5:
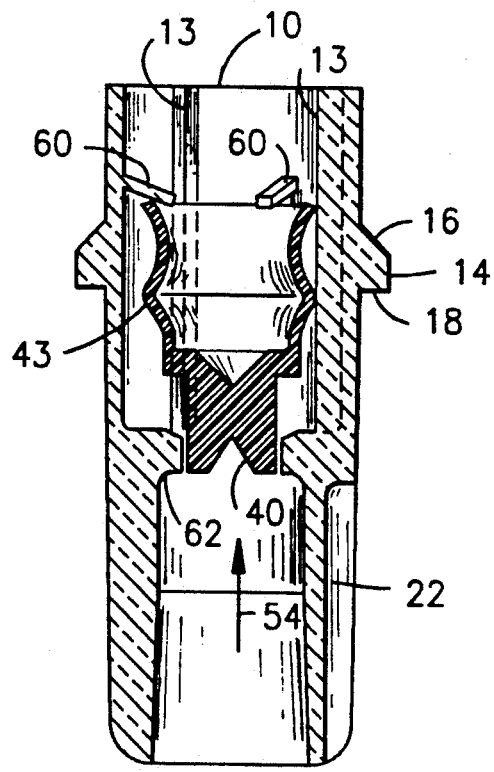
FIG. 5 is a sectional view similar to FIG. 2, but showing the check valve in its axially displaced, distorted configuration.
Figure 6:
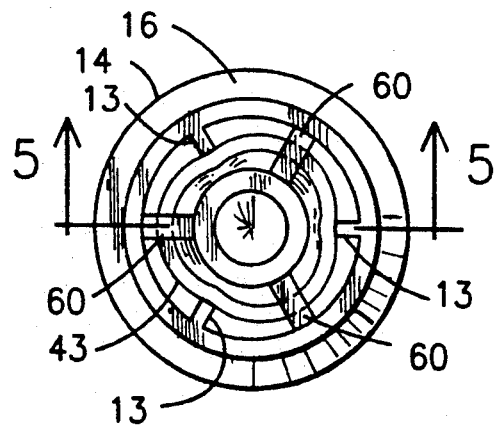
FIG. 6 is an end view similar to FIG. 4 showing the configuration of FIG. 5.

As indicated in FIG. 5, when a Luer fitting is introduced into cylindrical cavity 52 of the second part 20 of adapter 0, its leading end drives valve 40 in the direction of arrow 54, thereby unseating valve 40 and allowing fluid flow in the direction of arrow 54, i.e., into the catheter. Tubular walls 43 of valve 40 become distorted as shown in FIGS. 5 and 6 because a plurality of radially inwardly extending fingers, collectively denoted 60, formed on the inner cylindrical side walls of part 12 as shown in FIGS. 2 and 5, prevent axial displacement of said valve 40 when the Luer fitting bears against it. Valve 40 is of resilient, elastomeric construction and therefore springs back into its FIG. 2 shape as soon as the Luer fitting is withdrawn, thereby again preventing flow of fluid in the direction of arrow 41.

The manner of operation of valve 40 is well known. Longitudinally-extending, circumferentially-spaced, radially-inwardly protruding ribs 13 formed on the inner cylindrical sidewall of part 12 prevent the valve from assuming an airflow-blocking position. Those familiar with valves of this type will also appreciate that the small space between the leading end of valve 40 and the valve body, shown substantially at the center of both FIGS. 2 and 5, allows air to pass through the valve, as indicated by directional arrow 54 in FIG. 5 as aforesaid.

Annular shoulder 62 prevents over-insertion of the fitting; thus, the leading end of valve 40 is flush with annular shoulder 62 when the Luer fitting is fully inserted, as shown in FIG. 5. This prevents over-distortion of valve 40.

Prior art adapters lacked shoulder 62 and as a result, the distortion of valve 40 could be so great that said valve would fail to spring back into its undistorted position of repose. Such a failure may result in catastrophic leakage of anesthesia or other substance during surgical procedures. The present invention therefore overcomes the two major shortcomings of earlier adapters. It snugly fits Luer fittings of all sizes and it is not subject to failure arising from failure of check valve 40 to resume its position of repose upon withdrawal of the Luer fitting.

It is therefore clear that this invention is new and useful. Moreover, it was not obvious to those of ordinary skill in this art at the time it was made in view of the prior art considered as a whole.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An adapter having utility in connection with Luer fittings and similar fittings, comprising:

a tubular base member having a first generally tubular part adapted for substantially non-retractable slide fit engagement within a catheter, and a second generally tubular part adapted to slide fittingly receive a rigid, cylindrical-in-configuration fitting member;

said first and second parts being integrally formed with one another, being made of an elastomeric material, and having a common longitudinal axis of symmetry;

said second part having cylindrical side walls of predetermined thickness;

a plurality of longitudinally extending grooves of predetermined depth being formed in said second part;

each of said grooves having a common predetermined circumferential extent and a common depth, said grooves being circumferentially and substantially equidistantly spaced about said second part, and said second part having a predetermined thickness, where each groove is formed therein, that is less than said predetermined thickness of said cylindrical side walls;

a plurality of substantially equidistantly spaced ungrooved areas of said second part being defined between said grooves, said grooves and ungrooved areas alternating about the circumference of said second part, said ungrooved areas having a common circumferential extent that is substantially equal to the common circumferential extent of said grooves, and said ungrooved areas having a thickness substantially greater than the thickness of said grooved parts so that said ungrooved areas do not expand as do said grooved parts upon insertion of a fitting into said second part;

a slidably mounted check valve being disposed within said base member;

said alternating ungrooved areas being substantially non-expandable and thus countering the expendability of said grooves so that a tight fit is maintained even when said grooves are expanded;

said second part expanding radially outwardly as a whole upon insertion thereinto of a fitting due to said alternating arrangement of grooves and ungrooved areas of common circumferential extent about the circumferential extent of said second part;

whereby said grooves enable radially outward expansion of said second part when a fitting member is inserted therein, said second part having a greater circumference when expanded radially outward relative to its circumference when in repose.

2. The adapter of claim 1, wherein said plurality of grooves are equidistantly and circumstantially spaced apart so that said radially outward expansion is substantially uniform in all directions.

3. The adapter of claim 1, further comprising a plurality of radially inwardly extending fingers formed in an interior side wall of said first part for holding said check valve against axial displacement when a fitting member is introduced into said second part.

4. The adapter of claim 1, further comprising a radially-inwardly extending annular shoulder formed in said second part, said shoulder limiting the depth of insertion of said fitting member so that said check valve cannot be distorted beyond its elastic limit.

* * * * *